United States Patent
Han et al.

(10) Patent No.: US 11,782,053 B2
(45) Date of Patent: *Oct. 10, 2023

(54) IDENTIFICATION OF ANTIGEN-SPECIFIC ADAPTIVE IMMUNE RESPONSES USING ARM-PCR AND HIGH-THROUGHPUT SEQUENCING

(71) Applicant: iRepertoire, Inc., Huntsville, AL (US)

(72) Inventors: Jian Han, Huntsville, AL (US); Miranda Byrne-Steele, Huntsville, AL (US)

(73) Assignee: iRepertoire, Inc., Huntsville, AL (US)

( * ) Notice: Subject to any disclaimer, the term of this patent is extended or adjusted under 35 U.S.C. 154(b) by 140 days.

This patent is subject to a terminal disclaimer.

(21) Appl. No.: 14/348,483

(22) PCT Filed: Sep. 28, 2012

(86) PCT No.: PCT/US2012/058128
§ 371 (c)(1),
(2) Date: Mar. 28, 2014

(87) PCT Pub. No.: WO2013/049727
PCT Pub. Date: Apr. 4, 2013

(65) Prior Publication Data
US 2014/0235497 A1   Aug. 21, 2014

Related U.S. Application Data

(60) Provisional application No. 61/540,454, filed on Sep. 28, 2011.

(51) Int. Cl.
*C40B 30/04* (2006.01)
*G01N 33/53* (2006.01)
(Continued)

(52) U.S. Cl.
CPC ............ *G01N 33/53* (2013.01); *C07K 16/00* (2013.01); *C07K 16/1018* (2013.01);
(Continued)

(58) Field of Classification Search
None
See application file for complete search history.

(56) References Cited

U.S. PATENT DOCUMENTS

| 7,999,092 B2 | 8/2011 | Han |
| 2007/0269868 A1 | 11/2007 | Jensen et al. |

(Continued)

FOREIGN PATENT DOCUMENTS

| WO | 2009137255 | 11/2009 |
| WO | 2011146514 | 11/2011 |
| WO | 2013049727 | 4/2013 |

OTHER PUBLICATIONS

Esin et al. (Aug. 1, 1999) Infection and Immunity vol. 67 pp. 3800 to 3809.*

(Continued)

*Primary Examiner* — Christian C Boesen
(74) *Attorney, Agent, or Firm* — Butler Snow LLP; Matthew J. Parker (57) ABSTRACT

Disclosed is a method for correlating at least one amino acid sequence from an antibody isolated from human or animal blood with at least one DNA sequence corresponding to the antibody in the immunorepertoire of the human or animal. The method also provides a means for pairing heavy and light chains to produce synthesized monoclonal antibodies.

2 Claims, 4 Drawing Sheets

Specification includes a Sequence Listing.

(51) Int. Cl.
- C07K 16/00 (2006.01)
- C07K 16/10 (2006.01)
- C12Q 1/6874 (2018.01)
- G01N 33/569 (2006.01)

(52) U.S. Cl.
CPC ............ *C12Q 1/6874* (2013.01); *C40B 30/04* (2013.01); *G01N 33/56966* (2013.01); *C07K 2317/21* (2013.01); *C07K 2317/55* (2013.01)

(56) References Cited

U.S. PATENT DOCUMENTS

| | | |
|---|---|---|
| 2010/0021896 A1 | 1/2010 | Han |
| 2010/0137151 A1 | 6/2010 | Emili et al. |
| 2010/0239548 A1 | 9/2010 | Zang |
| 2010/0322910 A1 | 12/2010 | Kammula |

OTHER PUBLICATIONS

Wang et al. (Jan. 4, 2010) Proceedings of the National Academy of Sciences USA vol. 107 pp. 1518 to 1523.*

Altman, J.D., et al. Phenotypic analysis of antigen-specific T lymphocytes. Science. 1996. 274: 94-96. J Immunol 187, 7-9.

Bubeck, P., Winkler, M., and Bautsch, W. (1993). Rapid cloning by homologous recombination in vivo. Nucleic Acids Res 21, 3601-3602.

Esin, S. et al. (1999). In Vitro Expansion of T-Cell-Receptor V[alpha]2.3+ CD4+ T Lymphocytes in HLA-DR17(3), DQ2+ Individuals upon Stimulation with Mycobacterium tuberculosis. Infection and Immunity 3800-3809.

Jacquemin, M., et al. (2006). Variable region heavy chain glycosylation determines the anticoagulant activity of a factor VIII antibody. J Thromb Haemost 4, 1047-1055.

Jiang, X., et al. (2002). Expression of Fab fragment of catalytic antibody 6D9 in an *Escherichia coli* in vitro coupled transcription/translation system. FEBS Lett 514, 290-294.

Jin, A., et al. (2009), A rapid and efficient single-cell manipulation method for screening antigen-specific antibody- secreting cells from human peripheral blood. Nat Med 15, 1088-1092.

Kohler, G., and Milstein, C. (1975). Continuous cultures of fused cells secreting antibody of predefined specificity. Nature 256, 495-497.

Marsic, D., et al. (2008). PCR-based gene synthesis to produce recombinant proteins for crystallization. BMC Biotechnol 8, 44.

Oliner, J.D., Kinzler, K.W., and Vogelstein, B. (1993). In vivo cloning of PCR products in *E. coli*. Nucleic Acids Res 21, 5192-5197.

Pansri, P., et al. (2009). A compact phage display human scFv library for selection of antibodies to a wide variety of antigens. BMC Biotechnol 9, 6.

Reichert, J.M., et al. (2005). Monoclonal antibody successes in the clinic. Nat Biotechnol 23, 1073-1078.

Wang, C., et al. (2010). High throughput sequencing reveals a complex pattern of dynamic interrelationships among human T cell subsets. Proc Natl Acad Sci USA 107, 1518-1523.

Zhu, D., et al. (2002). Acquisition of potential N-glycosylation sites in the immunoglobulin variable region by somatic mutation is a distinctive feature of follicular lymphoma. Blood 99, 2562-2568.

Byrne-Steele, et al., "Development of an alternative methods for the identification and production of antigen-specific monoclonal antibodies," Hudson Alpha Institute for Biotechnology, 2011.

BioOnline, Screening to Obtain Single Chain Antibodies (scFV) with Optimized Disassociating Rate, http://www.bioon.com.cn/sub/showarticle.asp?Newsid=16200, published on Nov. 16, 2009.

* cited by examiner

| BYRNE-STELLE_A1_091310_igpep | | |
|---|---|---|
| Scan No. | Peptide Mass | Peptide Sequence | Sequence Header |
| 3344 | 2424.19 | ESTYYNWGQGTLVTVSSASTK | >gi|xxxxxxxx|CP0_IGH_GJQGNIM91EKNU5 |
| 2912 | 1367.72 | NTLYLQMNSLR | >gi|xxxxxxxx|J3M7_IGH_GMPTOXV01A70ID |
| 3344 | 2424.27 | VVRGYKSNWGQGTLVTVSSASTK | >gi|xxxxxxxx|J3M7_IGH_GMPTOXV03HNMK |
| 3008 | 1835.81 | DWGQGTLVTVSSASTK | >gi|xxxxxxxx|C2M21_IGH_GMNM01S01BJK0M |
| 2716 | 1331.61 | AEDTAVYYCK | >gi|xxxxxxxx|C2M21_IGH_GMNM01S01BR76P |
| 2716 | 1331.61 | AEDTAVYYCLK | >gi|xxxxxxxx|C2M21_IGH_GMNM01S01CWUQL |

| BYRNE-STELLE_B1_091310_igpep | | |
|---|---|---|
| Scan No. | Peptide Mass | Peptide Sequence | Sequence Header |
| 2890 | 1916.93 | NYIAWYQQKPGQPPK | >gi|xxxxxxxx|C2M21_IGK_GMNM01S01DQ2IJ |
| 2850 | 1302.81 | FSGSGSGTDFTLK | >gi|xxxxxxxx|C2M21_IGK_GMNM01SD2GCF4J |
| 3034 | 1631.78 | FSGSGSGTDFTLTISR | >gi|xxxxxxxx|C2M21_IGK_GMNM01SO1C4R05 |
| 2914 | 1218.66 | SGTSASLAISGLR | >gi|xxxxxxxx|CP21_IGL_GJQGNIM2FZP7F |
| 3084 | 2042.03 | ANPTVTLFPPSSEELQANK | >gi|xxxxxxxx|F2_8n_IGL_FWHENJ01BJJ8W |

```
                         SEQUENCE LISTING

<160> NUMBER OF SEQ ID NOS: 11

<210> SEQ ID NO 1
<211> LENGTH: 22
<212> TYPE: PRT
<213> ORGANISM: Homo sapiens

<400> SEQUENCE: 1

Ser Tyr Asn Tyr Val Asn Tyr Trp Gly Gln Gly Thr Leu Val Thr Val
1               5                   10                  15

Ser Ser Ala Ser Thr Lys
            20

<210> SEQ ID NO 2
<211> LENGTH: 11
<212> TYPE: PRT
<213> ORGANISM: Homo sapiens

<400> SEQUENCE: 2

Asn Thr Leu Tyr Leu Gln Phe Asn Ser Leu Arg
1               5                   10

<210> SEQ ID NO 3
<211> LENGTH: 23
<212> TYPE: PRT
<213> ORGANISM: Homo sapiens

<400> SEQUENCE: 3

Val Val Arg Gly Tyr Lys Ser Asn Trp Gly Gln Gly Thr Leu Val Thr
1               5                   10                  15

Val Ser Ser Ala Ser Thr Lys
            20

<210> SEQ ID NO 4
<211> LENGTH: 16
<212> TYPE: PRT
<213> ORGANISM: Homo sapiens

<400> SEQUENCE: 4

Asp Trp Gly Gln Gly Thr Leu Val Thr Val Ser Ser Ala Ser Thr Lys
1               5                   10                  15

<210> SEQ ID NO 5
<211> LENGTH: 11
<212> TYPE: PRT
<213> ORGANISM: Homo sapiens

<400> SEQUENCE: 5

Ala Glu Asp Thr Ala Val Tyr Tyr Cys Ile Lys
1               5                   10

<210> SEQ ID NO 6
<211> LENGTH: 11
<212> TYPE: PRT
<213> ORGANISM: Homo sapiens

<400> SEQUENCE: 6

Ala Glu Asp Thr Ala Val Tyr Tyr Cys Leu Lys
1               5                   10
```

```
<210> SEQ ID NO 7
<211> LENGTH: 15
<212> TYPE: PRT
<213> ORGANISM: Homo sapiens

<400> SEQUENCE: 7

Asn Tyr Ile Ala Trp Tyr Gln Gln Lys Pro Gly Gln Pro Pro Lys
1               5                   10                  15

<210> SEQ ID NO 8
<211> LENGTH: 13
<212> TYPE: PRT
<213> ORGANISM: Homo sapiens

<400> SEQUENCE: 8

Phe Gly Ser Ser Gly Ser Gly Thr Asp Phe Thr Leu Lys
1               5                   10

<210> SEQ ID NO 9
<211> LENGTH: 16
<212> TYPE: PRT
<213> ORGANISM: Homo sapiens

<400> SEQUENCE: 9

Phe Gly Ser Ser Gly Ser Gly Thr Asp Phe Thr Leu Thr Ile Ser Arg
1               5                   10                  15

<210> SEQ ID NO 10
<211> LENGTH: 13
<212> TYPE: PRT
<213> ORGANISM: Homo sapiens

<400> SEQUENCE: 10

Ser Gly Thr Ser Ala Ser Leu Ala Ile Ser Gly Leu Arg
1               5                   10

<210> SEQ ID NO 11
<211> LENGTH: 19
<212> TYPE: PRT
<213> ORGANISM: Homo sapiens

<400> SEQUENCE: 11

Ala Asn Pro Thr Val Thr Leu Phe Pro Pro Ser Ser Glu Glu Leu Gln
1               5                   10                  15

Ala Asn Lys
```

IDENTIFICATION OF ANTIGEN-SPECIFIC ADAPTIVE IMMUNE RESPONSES USING ARM-PCR AND HIGH-THROUGHPUT SEQUENCING

PRIORITY CLAIM

This application claims the benefit of priority of earlier-filed U.S. Provisional Patent Application No. 61/540,454, filed Sep. 28, 2011. The contents of U.S. Provisional Patent Application No. 61/540,454 are incorporated herein by reference, where allowed by applicable law and regulation.

FIELD OF THE INVENTION

The invention relates to methods for the identification of antigen-specific adaptive immune responses.

BACKGROUND OF THE INVENTION

Monoclonal antibodies (mAbs) are widely used in applications ranging from diagnostic and research agents to therapeutic pharmaceuticals. A critical step in the production of medically useful antibodies (Abs) is the initial identification of the desired antigen-specific Abs. This is usually performed using multiple rounds of "panning" in techniques such as hybridoma and phage display or by ELISPOT in chip-based methods such as ISAAC (Jin, A., et al. (2009), A rapid and efficient single-cell manipulation method for screening antigen-specific antibody-secreting cells from human peripheral blood. *Nat Med* 15, 1088-1092).

An immune repertoire is comprised of all of the functionally diverse B and T cells in circulation at any given moment and is largely influenced by both genetic and environmental factors such as HLA type and antigen exposure history.

The diverse antigen receptors of T and B lymphocytes are produced by somatic recombination of a limited, but very large number of gene segments. These gene segments: V (variable), D (diversity), J (joining), and C (constant), determine the binding specificity of immunoglobulins and T cell receptors (TCRs).

The first and most common method for producing monoclonal antibodies was developed by Kohler and Milstein in 1975. In this method, a mouse is immunized by injection of an antigen to stimulate the production of antigen-specific antibodies. Individual antibody-forming cells are isolated from the mouse's spleen and fused with immortal myeloma cells to produce hybridomas (Kohler, G., and Milstein, C. (1975). Continuous cultures of fused cells secreting antibody of predefined specificity. *Nature* 256, 495-497). The antibodies secreted by each of the different clones are assayed for their antigen-binding ability using well-established methods such as ELISA. The most stable and productive clones are mass-produced by using either in vitro cell-culture techniques or by injecting them into the peritoneal cavity of a mouse, where the hybridoma secretes the monoclonal antibodies as ascitic fluid.

Hybridoma technology has historically been time-consuming and labor-intensive, and the resulting hybridomas may be genetically unstable (Chambers, R. S. (2005). High-throughput antibody production. *Curr Opin Chem Biol* 9: 46-50.). Furthermore, if the hybridomas are propagated in the mouse, too much ascitic fluid can accumulate, likely producing pain and distress for the animal. The therapeutic success rate of antibodies derived from mouse hybridomas has historically been low due to the high immunogenicity the foreign proteins elicit in humans (Carter, P. J. (2006). Potent antibody therapeutics by design. *Nat Rev Immunol* 6, 343-357; Reichert, J. M., et al. (2005). Monoclonal antibody successes in the clinic. *Nat Biotechnol* 23, 1073-1078.). Additional steps such as chimerization or humanization are often required to make the antibodies useful for therapeutic purposes. Chimerization involves joining the variable domain (the antigen-binding domain) of the mouse with the constant domains of a human antibody, while humanization involves grafting the complementary determining regions (CDRs; antigen-binding loops in the variable domain) from a mouse antibody onto a human IgG. Oftentimes, the "humanized" IgG does not bind the antigen with the same affinity as the original mouse antibody because the framework regions flanking the grafting site often contribute to the proper CDR conformation required for binding (Kipriyanov, S. M., and Le Gall, F. (2004). Generation and production of engineered antibodies. *Mol Biotechnol* 26, 39-60). Other methods have been developed for the production of completely human antibodies, and many of the antibodies currently entering clinical trials are completely human (Carter, P. J. (2006). Potent antibody therapeutics by design. *Nat Rev Immunol* 6, 343-357). Typically, they are derived from either transgenic mice capable of expressing human immunoglobulin genes (and produced using hybridoma technology), or they are derived from phage-display technology (Carter, P. J. (2006). Potent antibody therapeutics by design. *Nat Rev Immunol* 6, 343-357). With phage-display technology, antibody genes are expressed and displayed on the surface of filamentous bacteriophage as fusion proteins. The displayed antibody genes are often isolated from B-lymphocytes of non-immunized donors, creating a naïve library that can be utilized as a valuable source of human antibodies against various antigens (Pansri, P., et al. (2009). A compact phage display human scFv library for selection of antibodies to a wide variety of antigens. *BMC Biotechnol* 9, 6).

A phage display antibody library is a collection of phages, each phage particle displaying a single antibody on its surface. The phage library must be panned, often repeatedly, in order to identify high affinity antigen-specific clones. Furthermore, because the phage display library depends upon the in vitro selection of an appropriate antibody, the library must cover at least $10^8$ individual clones.

The application of high-throughput sequencing to immune repertoire analysis is relatively new and very powerful. For instance in 2009, one sequencing run produced far more unique CDR3 sequences than accumulated throughout the entire lifetime of the NCBI (Wang, C., et al. (2010). High throughput sequencing reveals a complex pattern of dynamic interrelationships among human T cell subsets. *Proc Natl Acad Sci USA* 107, 1518-1523). What are needed are methods for using high throughput sequencing for analysis of the immune response and for manipulation of the response for the purpose of treating disease.

SUMMARY OF THE INVENTION

The present invention relates to a method for identifying antibodies that are specific for a given antigenic entity, the method comprising isolating at least one antigen-specific antibody from a blood or tissue sample obtained from a human or animal subject, determining an amino acid sequence (e.g., a peptide sequence) of the at least one antigen-specific antibody, and comparing the amino acid (peptide) sequence of the at least one antigen-specific antibody with a sequence database comprising an immunorepertoire from the human or animal subject to identify antigen-specific clonally-expanded antibody sequences, and cloning and expressing the antigen-specific clonally-expanded antibody sequences to associate heavy and light chains which bind with specificity to at least one target antigen or epitope thereof.

The invention also provides a method for identifying antigen-specific T cells, the method comprising isolating peripheral blood mononuclear cells (PBMC) from a sample of human or animal blood, splitting the PBMC into at least two subsets (one control subset that will receive no antigen and an experimental subset that will receive an empirically determined amount of antigen), culturing the PBMC in vitro, adding an effective amount of a target antigen to the PBMC in vitro at the start of culture, harvesting the PBMCs at an empirically determined time after adding the target antigen, producing an arm-PCR sequenced immunorepertoire from the harvested PBMC (both T cell repertoire and B cell repertoire from stimulated and unstimulated subsets), and comparing that immunorepertoire to the arm-PCR sequenced immunorepertoire prepared from isolated PBMC from the same subject to which target antigen has not been added, and identifying the T cells which have expanded based upon their increased numbers in the T cells to which antigen has been added, as compared to the T cells to which no antigen was added.

A similar method may be applied to identify antigen-specific B cell responses from the same experiment. The B cell repertoire from both the stimulated and unstimulated samples are compared to identify clonally expanded populations responding to the antigen. In addition, any secreted antigen-specific antibodies may be purified from the in vitro media and identified by utilizing LC mass spectrometric peptide matching to the unstimulated or stimulated repertoires. In various aspects of the invention as it may be applied specifically
to antibodies and B cells, a step may be added—that step comprising cloning and expressing heavy and light chain pairs to match heavy and light chain binding pairs which bind with specificity to at least one target antigen.

DETAILED DESCRIPTION

The inventors have developed a new method that allows for the rapid and direct identification of antigen-specific adaptive immune responses from an organism using a method that couples amplicon rescued multiplex PCR (arm-PCR, described in U.S. Pat. No. 7,999,092) with high-throughput immune repertoire sequencing in conjunction with liquid chromatography tandem mass spectrometry (LC MS/MS). The invention utilizes arm-PCR and high-throughput sequencing to create a sequence database of the V(D)J rearrangements of B and T cell receptors. The V-region (or antigen-specific portion) of purified antigen-specific antibodies is then identified using mass spectrometric peptide mapping against the high-throughput sequencing database. The invention also provides methods for obtaining antigen-specific repertoire information by comparing T and B cell repertoires before and after antigen exposure both in vivo and in vitro.

In various aspects, the invention relates to a method for identifying antibodies that are specific for a given antigenic entity, the method comprising isolating at least one antigen-specific antibody from blood serum obtained from a human or animal subject, obtaining an amino acid sequence (peptide sequence) from the at least one antigen-specific antibody, and comparing the amino acid sequence of the at least one antigen-specific antibody with a sequence database comprising an immunorepertoire from the human or animal subject to identify antigen-specific clonally-expanded antibody sequences, and cloning and expressing the antigen-specific clonally-expanded antibody sequences to associate heavy and light chains which bind with specificity to at least one target antigen or epitope thereof.

The invention also provides a method for identifying antigen-specific T cells, the method comprising obtaining a sample of blood from a subject that has been previously challenged with antigen in vivo, isolating T cells from the sample and culturing the T cells in vitro, adding an effective amount of a target antigen to the T cells in vitro, harvesting the T cells at an empirically determined time point after adding the target antigen, producing an arm-PCR sequenced immunorepertoire from the harvested T cells, comparing that immunorepertoire to an arm-PCR sequenced immunorepertoire prepared from isolated T cells from the same subject to which target antigen has not been added, and identifying the T cells which have expanded based upon their increased numbers in the T cells to which antigen has been added, as compared to the T cells to which no antigen was added.

In various aspects of the invention as it may be applied specifically to antibodies and B cells, a step may be added—that step comprising cloning and expressing heavy and light chain pairs to match heavy and light chain binding pairs which bind with specificity to at least one target antigen. In addition, any secreted antigen-specific antibodies may be purified from the in vitro media and identified by utilizing LC mass spectrometric peptide matching to the unstimulated or stimulated repertoires "Antigenic entity," as used herein, is, for example, an antigen, an antigenic substance, a microbe, such as a bacterium or virus, etc., which comprises one or more antigens or epitopes that are recognized by the immune system of a human and/or animal. An "immunorepertoire," as used herein, is a database comprising DNA and/or protein sequences of the detectable variable region gene rearrangements in a blood sample comprising T and/or B cells of an individual human or animal subject. In various aspects of the invention, an immunorepertoire is obtained as described in United States Patent Application Publication Number US20100021896, which may, for example, be produced using a method known as arm-PCR (described in U.S. Pat. No. 7,999,092). The application of high-throughput sequencing to produce hundreds of thousands of sequencing reads from T cells, for example, has been described by Wang, et al. (Wang, C. et al., High throughput sequencing reveals a complex pattern of dynamic interrelationships among human T cell subsets, *Proc Natl Acad Sci USA*. 2010 Jan. 26; 107(4):1518-23).

Previous attempts to identify antigen-specific T cells in vitro have been hampered by the lack of sensitivity and specificity of many assay techniques. T cell receptors (TCR) are quite different from B cell receptors (BCR) in several aspects. First, the TCR is membrane bound and does not appear in soluble form as the BCR does. Hence, quite complex cellular assays are required to determine TCR specificity. Second, in the absence of additional protein complexes such as MHC, TCR have a low binding affinity for their target substrates, whereas antibodies and BCR bind their substrates tightly without any additional aid. TCR require the aid of the MHC complex in order to bind and recognize their cognate antigen. The MHC carries with it a peptide of the original antigen and presents it to the TCR. Currently, the most common method for the identification of antigen-specific TCR is the MHC tetramer method. In this method, recombinant MHC are biotinylated and folded with the peptide of interest. The MHC are tetramerized by a fluorescently labeled streptavidin. The tetramer will specifically label T cells that express the TCR receptors specific for a given peptide-MHC complex. Tetramers are required because the binding between a single TCR and a single MHC molecule is weaker, while a tetramer can bind to three TCRs at once (Altman, J. D., Moss, P. A., Goulder, P. J., Barouch, D. H., McHeyzer-Williams, M. G., Bell, J. I., McMichael, A. J., and Davis, M. M. Phenotypic analysis of antigen-specific T lymphocytes. Science. 1996. 274: 94-96. J Immunol 187, 7-9.).

Identification of antigen-specific T cells would, however, provide valuable information for the diagnosis of disease. For example, T cells identified to be associated with a particular disease state, based upon the method of the invention, could readily be used as a marker for the presence of a disease in another individual for whom a diagnosis has not yet been made. Identification of T cells which are associated with specific antigens, based upon their proliferation in response to antigenic challenge in vivo or in vitro using the method of the invention, could also provide a physician with confirmation that an individual has subclinical disease which has not produced significant symptoms at the time of an office visit, for example.

The needed specificity and sensitivity is provided by the use of arm-PCR sequencing for producing an immunorepertoire comprising the sequences represented by the various T-cell receptor genetic rearrangements within the T cell population sampled. In order to identify cells which may have been present at higher or lower percentages in the original in vitro T cell population, but have proliferated in response to antigen, arm-PCR provides a semi-quantitative result that allows comparison of the relative numbers of cells, as represented by the detected sequences. By identifying the sequences that represent T cells whose populations have increased significantly after in vitro antigen challenge, it is possible to identify the T cell receptor sequences, and therefore the associated T cells, that participate in the cellular immune response to a particular antigenic entity.

In the method of the invention, PBMC (which contain T cells and B cells) obtained from a blood sample from a single patient are stimulated with an antigen, or epitope thereof, in vitro to produce recall memory and proliferation, then the T cell population within that sample, as represented by the sequences amplified and detected by a method that employs arm-PCR sequencing, is compared to sequences amplified and detected from a T cell population of a blood sample from the same individual patient which has not been subjected to in vitro challenge by the same antigen or epitope.

The first step in isolating antigen-specific antibodies, specifically IgG, is by purifying the general IgG from the blood serum in order to remove any contaminating serum albumin and other blood serum proteins, which can result in lower yields of antigen-specific IgG downstream. There are many ways that this can be performed, including but not limited to for example, ammonium sulfate precipitation followed by size-exclusion chromatography, or directly by affinity chromatography as with Protein A, Protein G, or IgSelect, or by ion-exchange chromatography. After purifying the general IgG population, immunoaffinity purification is the most commonly used method to purify antigen-specific antibodies. Typically, immunoaffinity purification involves covalently cross-linking the antigen or epitope fragment of interest to a solid support. The solid support matrix typically is "activated" agarose, cross-linked agarose, polyacrylic, or magnetic beads, which are commericially available. Each has a different coupling mechanism that depends on the support matrix and vendor instructions. During immunoaffinity purification, the general IgG population is allowed to bind anywhere from one hour to overnight. The unbound antibodies are removed by washing, and the specific antibodies are eluted, typically by lowering the pH (the pH of the solution is restored immediately by adding a highly concentrated alkaline buffering solution). However, elution can be performed in a variety ways, for example, by adding harsher reagents such as 1.5 M potassium thiocyanate, 4 M urea, 3.5 M $MgCl_2$, or by using a gradient of low pH buffer solutions.

In various aspects of the invention, isolation of the general IgG population is performed using an affinity column such as the IgSelect column from GE Healthcare, as disclosed in the accompanying examples. The immunoaffinity purification of the antigen-specific population in the disclosed example is performed using a MicroLink Protein Coupling Kit from Thermoscientific/Pierce as per manufacturer's instructions. In this case, purified antigen-specific IgG were concentrated, and heavy and light chains separated by performing SDS-PAGE analysis under reducing conditions. In addition, some of the concentrated sample was applied to a Fab Micro Preparation kit to prepare Fab fragments. The Fab fragments were also applied to an SDS-PAGE gel under reducing conditions. Gel bands corresponding to the heavy chain, light chain, and Fab fragments were carefully excised in a manner to avoid keratin contamination. Analysis of the protein sequence of the isolated antibody/antibodies may be quickly and efficiently performed using liquid chromatography tandem mass spectrometry (LC/MS/MS), a technique which has been described previously in the literature. The immunorepertoire of the subject may be generated using techniques described in U.S. Pat. No. 7,999,092 and U.S. Patent Publication No. 20100021896, using primers disclosed in those publications, for example. Comparison of sequences generating using LC/MS/MS performed for a specific antibody or a small subset of antibodies and the immunorepertoire of the subject from which the antibodies are isolated may be performed by means known to those of skill in the art of data management and information technology. Comparing the sequences confirms the specific sequence and provides information related to the degree of clonal expansion at a given point in time, which may be especially helpful in the evaluation of vaccine response, for example. Cloning and expression to pair the corresponding heavy and light chains may be done using techniques known to those of skill in the art, and for which kits are readily available.

Identification of an antigen-specific antibody using the method of the invention enables a scientist to scale-up production of the appropriate heavy/light chain antibody combination to produce "monoclonal" antibodies having the same antigen-binding V-region protein sequence as those of the individual from whom the original cells were derived. While peripheral blood will often be the source of such cells, samples may be obtained using a variety of techniques and may include, for example, peripheral blood mononuclear cells, spleen, lymph node, etc. Sampling to obtain cells may be performed at various time points prior to or after exposure to antigen.

Heavy and light chain pairing information is lost during high throughput sequencing. To overcome this restriction, combinations of heavy and light chain pairs can be recombinantly expressed as Fab fragments in a grid pattern on a microtiter plate, and their binding against the antigen measured with ELISA. The expression can be performed in a human in vitro expression system using a plasmid representing the heavy chain ($F_D$) and a plasmid for the light chain (either κ or λ). However, any expression system, either in vitro, in vivo, or both, could be used including *E. coli*, mammalian expression systems such as Hek 293, yeast, and etc. In current aspects of the invention, cloning was performed using homologous recombination with the pT7CFE1-Chis vector included with the Human In Vitro Glycoprotein Expression kit from Thermoscientific/Pierce. The vector, which contains the essential elements for the in vitro expression of the gene targets, including a T7 promoter, internal ribosomal entry site (IRES), multiple cloning site (MCS), C-terminal 6×-His tag, poly A tail, and ampicillin resistance gene, was modified to also include a representative fourth framework region (FR4) and a C-region sequence for the heavy chain and both light chains (κ and λ), which the inventors termed "V-ready" cassettes (3 cassettes total: heavy, kappa, and lambda V-ready cassette). The FR4 is used as an overlapping area enabling the recombination of the V-region with the C-region of the V-ready cassette. The FR4 represents a consensus sequence in the region directly after the CDR3 as determined from sequence alignments available through the V-base database and aids in maintaining the proper three-dimensional structure of the CDR3, which has been implicated in antigen-specificity. An identified V-region can be readily inserted into the appropriate "V-ready" cassette by homologous recombination cloning (HRC) for downstream expression in the in vitro system as Fab fragments. HRC is based on the ability of many *E. coli* strains (including the RecA deficient ones used in cloning) to perform in vivo intermolecular recombination between DNA fragments sharing homologous sequences at their ends (Bubeck, P., Winkler, M., and Bautsch, W. (1993). Rapid cloning by homologous recombination in vivo. *Nucleic Acids Res* 21, 3601-3602; Jones, D. H., and Howard, B. H. (1991). A rapid method for recombination and site-specific mutagenesis by placing homologous ends on DNA using polymerase chain reaction. Biotechniques 10, 62-66; Oliner, J. D., Kinzler, K. W., and Vogelstein, B. (1993). In vivo cloning of PCR products in *E. coli*. *Nucleic Acids Res* 21, 5192-5197.). Gene fragments can be quickly subcloned into a linearized target plasmid vector without restriction digest, ligation, or other enzymatic manipulation (Marsic, D., Hughes, R. C., Byrne-Steele, M. L., and Ng, J. D. (2008). PCR-based gene synthesis to produce recombinant proteins for crystallization. *BMC Biotechnol* 8, 44.). The overlapping ends that match the V-ready cassettes are placed on the V-region by PCR with primers that include homologous sequences to the V-ready cassette. In the currently described design, a c-myc tag and FLAG tag were added to both the heavy and light chain V-regions, respectively, during PCR amplification to facilitate downstream detection of both expression and antigen-binding. Any type of cloning could be used to place a given V-region, $F_D$, heavy chain, or light chain sequence into a vector with the appropriate elements for in vitro expression; however, the inventors believe that the HRC method is the fastest and easiest solution for the current application. First, the method does not require restriction, which is important if a high-throughput approach is utilized to test many V-regions. Second, it is highly efficient and rapid. The inventors have witnessed a 95% positive insert rate with the correct sequence when used in conjunction with highly purified primers and a high fidelity polymerase such as Phusion from Finnzymes (when PCR amplifying the V-region). Third, the inventors have been able to create a seamless overlap between the V-region and C-region by designing the overlapping region directly adjacent to the restriction site but not including the site in the primer. This removes the additional amino acids in the final protein product that sometimes result due to the necessary presence of restriction sites in the vector.

Once expressed in the in vitro system, the protein can be purified using metal affinity chromatography and the His-tag on the protein. This can be performed in many numbers of ways; however, in the current description, Ni-NTA magenetic beads were utilized for their ease and speed. Binding can be confirmed using ELISA with a conjugated detection antibody against both the c-myc and FLAG tag. Once binding pairs are confirmed, they can be transferred relatively easily to other formats (scFv, full-length IgG, etc.), and production can be scaled to the application's requirements.

One significant advantage of the method of the present invention is that the antibodies have the potential to be entirely human, thus avoiding the immunogenicity encountered with mouse IgGs. This can be accomplished by sequencing the immune repertoire of a human sample and identifying the antigen-specific antibodies directly from that sample with mass spectrometric mapping, by comparing the repertoires before and after antigen administration, or by comparing repertoires of both challenged and unchallenged peripheral blood mononuclear cells after culturing in vitro. In addition, the antibodies will be produced recombinantly, avoiding the need for mouse hybridomas entirely.

The semi-quantitative nature of arm-PCR allows the identification of specific up-regulated clonal populations selected in vivo by a healthy immune system for a given antigen. In addition, since multiple exposures to an antigen refines the antibody response, this technology may utilize the inherent affinity maturation of the immune response and identify those clonally expanded populations that have the highest avidity for a specific antigen. Therefore, the rounds of panning required with phage display and the tedious screening of individual B cell clones in mouse hybridomas may be avoided.

Furthermore, the resultant repertoire database matches the sample from which the antibody was purified, which is not the case if comparing to a public database. When comparing an unchallenged repertoire versus a challenged repertoire (both in vitro and in vivo), the semi-quantitative nature of arm-PCR pinpoints specific differences that are potentially antigen related. Arm-PCR coupled with high-throughput sequencing and recent advances in pyrosequencing platforms makes this type of analysis possible.

This method has many additional possibilities. For instance, it may be possible to probe a naïve immune system for antigen-specific antibodies, thereby subverting the need for antigen administration. This would be convenient for human subjects, as not all antigens can be ethically administered. Furthermore, instead of purifying with a whole antigen, the antigen-specific antibodies could be purified with epitope fragments. This would allow the user to pull out only those epitope-specific antibodies that a user might be interested.

The invention may be further described by means of the following non-limiting examples.

EXAMPLES

Hemagglutinin (HA) is an antigenic glycoprotein found on the surface of influenza viruses and is used as a component of vaccines to initiate an immune response. The 2009-2010 formulation of Fluzone® contains 30 μg/ml HA of each of the following three viruses: A/Brisbane/59/2007, IVR-148 (H1N1), A/Uruguay/716/2007, NYMC X-175C (H3N2) (an A/Brisbane/10/2007-like virus), and B/Brisbane/60/2008. The 2009-2010 influenza vaccine Fluzone® was administered to two healthy volunteers, who reported feeling normal and well in the 30 day period prior to vaccination. Both the 2008-2009 and 2009-2010 vaccines contain essentially the same influenza A H1N1 and H3N2 antigens but different B-strain antigens. In order to test our method and provide the greatest probability of matching antigen-specific antibodies with the humoral repertoire sequencing results, we chose volunteers who had previously received the 2008-2009 influenza vaccine.

Sample Preparation

Blood samples were taken at four specific time points: day 0, prior to vaccine administration; day 3, memory B cell response to previously encountered antigens; day 7, activated and memory B cell response; and day 21, emergence of memory B cells in response to a newly encountered antigen. B cells were sorted into naïve, activated, and memory subtypes using appropriately labeled magnetic beads (Miltenyi Biotec). Isolated cells were resuspended in RNAprotect reagent and counted using a hemacytometer. RNA was extracted from the cells using an RNAeasy kit (Qaigen), and the blood serum from the four time points was stored at −80° C. ELISA was used to demonstrate the immunity of the serum (data not shown).

Antigen-Specific IgG Purification and LC MS/MS

Figure 1:
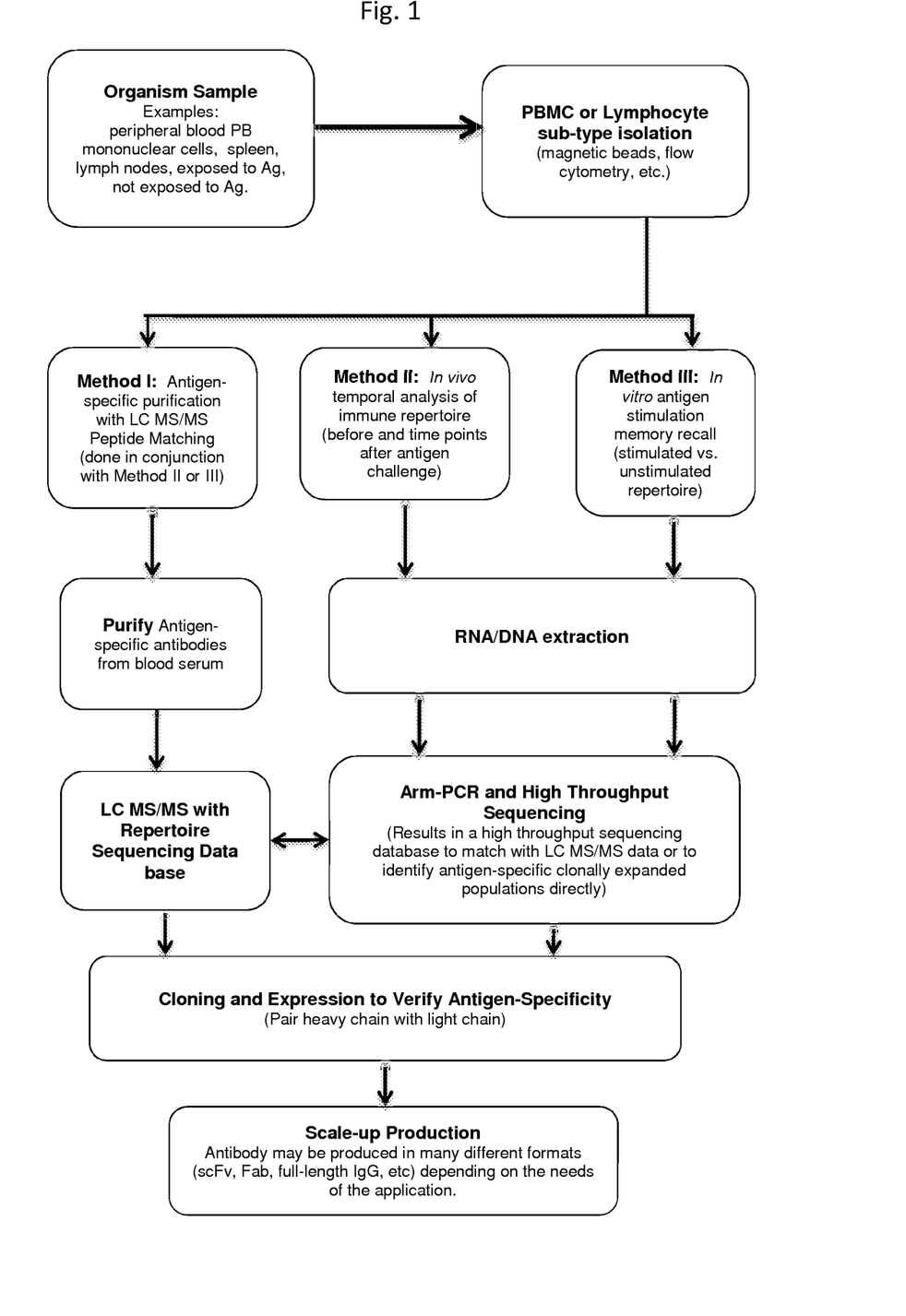
FIG. 1 is a diagram describing the various steps of the invention and certain modifications which allow it to be used more broadly in a variety of uses.
Figure 2:
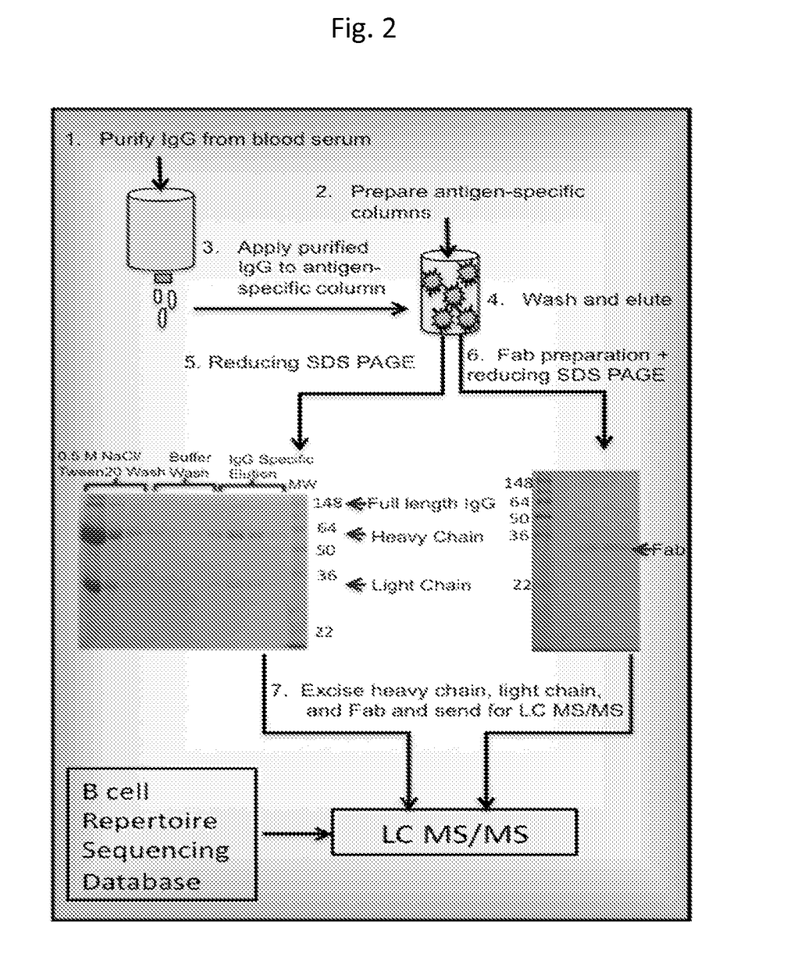
FIG. 2 is a diagram further describing the steps of the invention.

At this point, the study followed two parallel routes: (1) the antigen-specific IgG purification with LC mass spectrometry and (2) the B-cell repertoire analysis. The antigen-specific purification method is demonstrated in FIG. 1. Briefly, antigen-specific IgG was purified from day 3 and day 7 serum samples. Two-1 mL IgSelect columns (Ge-Healthcare) were used in order to purify the general IgG population from each of the individual's serum samples. Recombinant hemagglutinin A/Brisbane/59/2007 and A/Brisbane/10/2007 (SinoBiological Inc.) were covalently cross-linked separately to a micro spin-column using the MicroLink Protein Coupling kit (Pierce). A total of eight columns were produced: four for each individual with 2 antigen-specific columns per time point. Hence, each volunteer's specific antibody response to each antigen was assessed separately. Purified IgG (using an IgSelect column) was applied to the cross-link column, and the antigen-specific IgG population was eluted using low pH buffer. This process was repeated three times, and the elutions were pooled and concentrated. Fab fragments were also generated using a Fab Micropreparation kit (Pierce). Fab fragments were created due to concern that the abundance of constant domains in the heavy chain would obscure peptide matches to the variable region. The purified samples were analyzed under reducing conditions using SDS-PAGE analysis. The specific heavy chain, light chain, and Fab fragments against each influenza HA were excised from the gel and sent for protein identification using LC mass spectrometric peptide identification through ProtTech's protein identification service. During ProtTech's LC-MS/MS peptide sequencing, the excised band is treated with trypsin protease and concentrated 50-200 fold prior to injection into a HPLC, which then separates the peptide mixture. A tandem mass spectrometer is on-line coupled with the HPLC, and eluted peptides are fragmented by a process called collision-induced dissociation (CID). MS/MS spectra are acquired for each fragmented peptide (there are often several thousands MS/MS spectra from each sample). Each MS/MS spectrum (corresponding to a specific peptide sequence) is used to search the protein database for matched peptides. In our study, the B-cell repertoire gene sequencing results were used as a database for identification (see below).

Arm-PCR Amplification and High-Throughput Sequencing

For the B-cell repertoire analysis, the samples from both of the individuals were barcoded and pooled, so that the sequencing was performed in the same run. High-throughput sequencing using the Roche 454 Titanium sequencer allows for reads up to 400 bp. Therefore, sequence-specific primers were designed from the framework 1 region in the forward direction and the beginning of the C-region in the reverse for both the heavy and light chains. Consequently, the class-switch of specific B-cell clones can be monitored and their progression through memory response followed. Arm-PCR was performed, and the amplification products were sent to Seq-Wright for sequencing on the Roche 454 Titanium sequencer. The resulting 454 sequencing database of heavy and light chain V-regions was sent to ProtTech to serve as a database for matching peptides with the LC MS/MS spectra.

Peptide Sequencing Results

Figure 3:
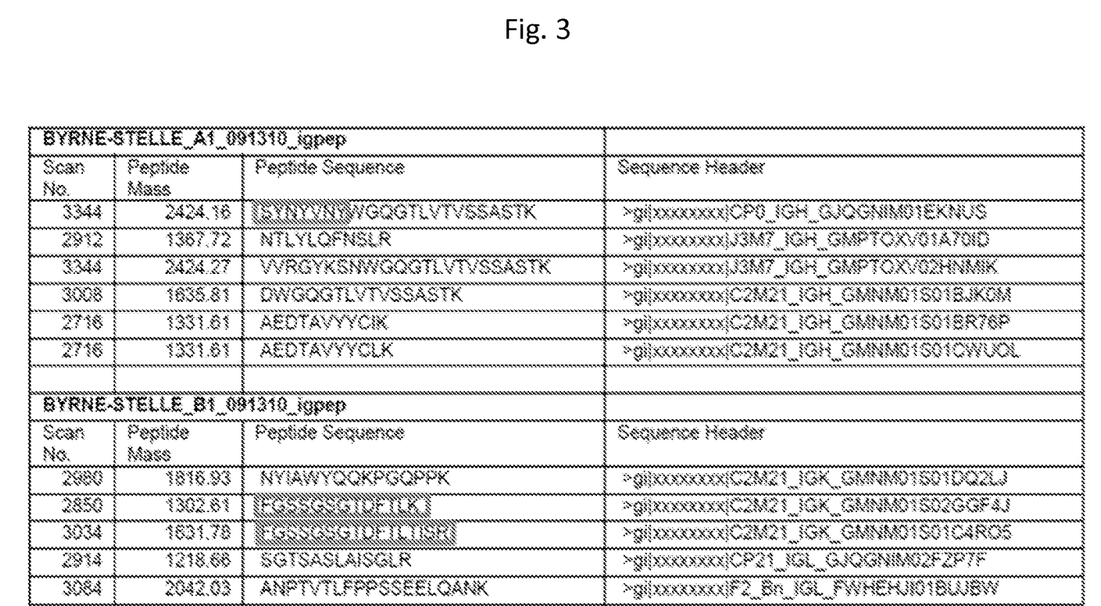
FIG. 3 is a table showing a sample of peptide sequences identified from antibody-producing cells obtained after challenge with Fluzone® (containing the hemagglutinin antigen of each of the following three viruses: A/Brisbane/59/2007, IVR-148 (H1N1), A/Uruguay/716/2007, NYMC X-175C (H3N2) (an A/Brisbane/10/2007-like virus), and B/Brisbane/60/2008).
Figure 4:
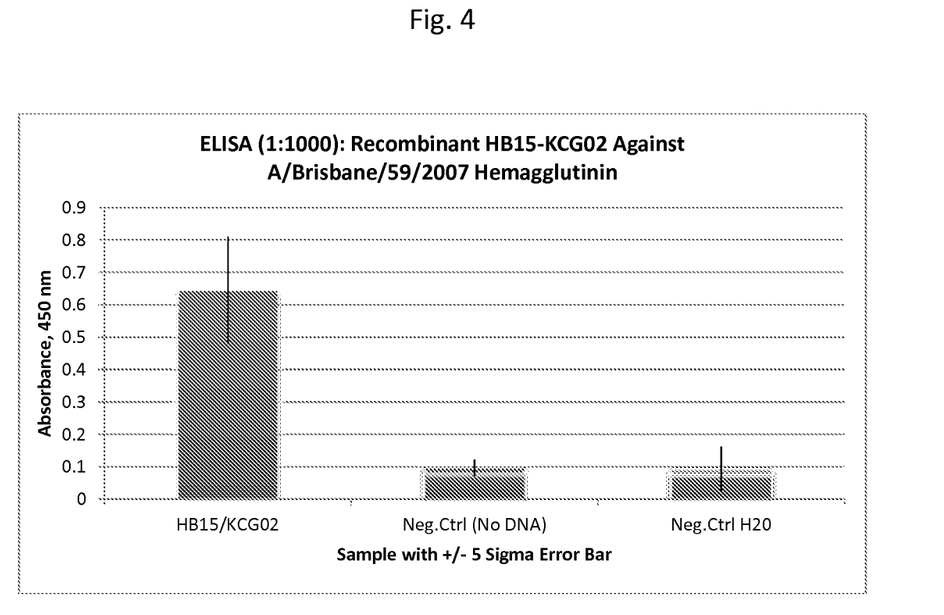
FIG. 4 is a graph representing results of an ELISA assay for an antigen-specific pair determined through LC MS/MS coupled to the repertoire database.

Several unique V-regions were successfully matched for each individual's response to both strains of influenza A. FIG. 3 represents a partial sample output of one individual's antigen-specific heavy chain and light chain response to A/Brisbane/59/2007 hemagglutinin. For instance, the first matching peptide in the list covers the entire CDR3 region of the heavy chain (highlighted in red), the fourth framework region, and the beginning of the C-region. This peptide is unique, matching to only one sequence in the entire database and corresponding to the correct individual. The entire VH sequence for >gi|xxxxxxxxx1CP0 IGH GJQGNIMO1EKNUS is not shown. What is shown is only the peptide used to match to the sequence. Furthermore, the second panel (B1) represents the light chain matches for the same antigen and individual. Two unique light chain matches were identified. The Fab results (for the same individual; data not shown) contain several additional unique heavy chain peptide matches, which would be expected since the response is polyclonal. Peptide sequences listed in FIG. 3 include SYNYVNYWGQGTLVTVS-SASTK (SEQ ID NO. 1), NTLYLOFNSLR (SEQ ID NO. 2), VVRGYKSNWGQGTLVTVSSASTK (SEQ ID NO. 3), DWGQGTLVTVSSASTK (SEQ ID NO. 4), AED-TAVYYCIK (SEQ ID NO. 5), AEDTAVYYCLK (SEQ ID NO. 6), NYIAWYQQKPGQPPK (SEQ ID NO. 7), FGSGSGSGTDFTLK (SEQ ID NO. 8), FGSSGSGTDFTLTISR (SEQ ID NO. 9), SGTSASLAIS-GLR (SEQ ID NO. 10), and ANPTVTLFPPSSEELQANK (SEQ ID NO. 11).

Since several unique peptides were successfully matched for each individual's response to both Flu A strains in the vaccine, we cloned and expressed these V-regions as Fab fragments to test their ability to bind influenza A antigen. As mentioned previously, a current issue with sequencing results is the inability to match a corresponding heavy chain with its light chain. To overcome this problem, we co-expressed different combinations of heavy chain and light chain plasmids directly on a microtiter plate. The human in vitro glycoprotein expression system from Pierce was selected for several reasons, although any recombinant system should suffice. However, the inventors believe the use of an in vitro system as described here provides several important advantages. First, an in vitro system provides an easy means for the co-expression of two plasmids simultaneously without concern about the transformation efficiency of one plasmid over the other (as with an in vivo system). For example, an *E. coli* in vitro transcription/translation system was utilized by Jiang et al. for the production of a Fab fragment to 6D9 using two separate plasmids: one for the heavy chain and one for light chain (Jiang, X., Ookubo, Y., Fujii, I., Nakano, H., and Yamane, T. (2002). Expression of Fab fragment of catalytic antibody 6D9 in an *Escherichia coli* in vitro coupled transcription/translation system. FEBS Lett 514, 290-294.). We have modified this concept to evaluate combinations of heavy and light chains plasmids added to a cell-free expression system in a 96-well format. An additional advantage to a cell-free system is the freedom from inclusion body formation that sometimes occurs when recombinant proteins are expressed in microbial cells. Since the gene targets in the described case are human in origin, a human expression system is best suited for their production. Furthermore, the proposed system produces glycoproteins, which is important because V-region glycosylation occurs in 10% of antibodies and can affect their antigen-binding ability (Jacquemin, M., Radcliffe, C. M., Lavend'homme, R., Wormald, M. R., Vanderelst, L., Wallays, G., Dewaele, J., Collen, D., Vermylen, J., Dwek, R. A., et al. (2006). Variable region heavy chain glycosylation determines the anticoagulant activity of a factor VIII antibody. J Thromb Haemost 4, 1047-1055.; Spiegelberg, H. L., Abel, C. A., Fishkin, B. G., and Grey, H. M. (1970). Localization of the carbohydrate within the variable region of light and heavy chains of human gamma g myeloma proteins. Biochemistry 9, 4217-4223.; Zhu, D., McCarthy, H., Ottensmeier, C. H., Johnson, P., Hamblin, T. J., and Stevenson, F. K. (2002). Acquisition of potential N-glycosylation sites in the immunoglobulin variable region by somatic mutation is a distinctive feature of follicular lymphoma. Blood 99, 2562-2568.). Finally, the expression system is fast, providing expressed proteins in less than 6 hours. The transcription/translation reaction is typically 25 µL and produces up to 40 µg/ml (1 µg total) of expressed protein, which is well above the detection limit of ELISA (0.0001-0.01 ug/ml). From an initial expression trial of 3 different heavy chains coupled with 3 different light chains (9 combinations), we have been able to identify two antigen-specific binding pairs. The in vitro system was used to scale-up the reaction so that binding could assayed in quadruplet measurements, and the binding was still evident as determined with ELISA and absorbance measurements at 450 nm. The heavy chain has an engineered N-terminal c-myc tag, while the light chain contains an N-terminal FLAG tag to facilitate detection in ELISA.

In Vitro or In Vivo Antigen-Stimulation Comparisons

In vivo stimulation comparisons refers to the temporal monitoring of an individual's immune repertoire on a set schedule. For example, time points might include but would not be limited to day 0, prior to antigen administration; day 3, memory B cell response to previously encountered antigens; day 7, activated and memory B cell response; and day 21, emergence of memory B cells in response to a newly encountered antigen. By sampling the immune repertoire at each of the time points, a molecular snapshot of the B cell and T cells in circulation can be taken prior to antigen challenge and at various time points after challenge. Expansion of specific clonal populations relative to the unstimulated sample may indicate a response to the antigen and can be verified by using the same recombinant expression strategy as was used during the previously described mass spectrometric method.

During in vitro stimulation, the antigenic memory of both the T cell and B cell repertoire is tested. In this experiment, PBMC are isolated from a blood sample and are cultured under appropriate conditions (see protocol) in both the presence and absence of antigen. The amount of antigen must be determined empirically. The situation in these types of experiments is different due to the inherent restriction of the beginning repertoire ($2 \times 10^6$ PBMCs). However, antigen-stimulation should result in the expansion and differentiation of the memory B cells into plasma cells. At an RNA level, the expansion of antigen-specific clones should be evident due to the semi-quantitative nature of arm-PCR and can be verified by using the same recombinant expression strategy as was described previously. Furthermore, secreted antibodies can be purified directly from the growth media (as with blood serum), and tandem LC MS/MS can be used for identifying the antibodies with the repertoire database as discussed previously. This type of experiment has the added benefit of being able to use any antigen of choice to stimulate the PBMC, including the use of antigens that would be unethical to administer in humans.

IgG Purification and Identification

IgGs were purified from human blood serum utilizing an IgSelect column from GEHealthcare. Binding Buffer (Equilibration Buffer)/Wash Buffer: 1×PBS (phosphate buffered saline) pH 7.4, (137 mM NaCl, 2.7 mM KCl, 10 mM sodium phosphate dibasic, 2 mM potassium phosphate monobasic and a pH of 7.4—pre-packaged). Elution Buffer: 100 mM glycine pH 3.0 or 100 mM sodium citrate pH 3.0. Neutralization Buffer: 1M Tris-HCl pH 9.0.

All flow rates were 0.5 ml/min (0.5 ml/min-1.0 ml/min), approximately 15 drops per minute (30 drops if rate is 1.0 ml/min). The column was equilibrated with 10 ml (10 CVs) of binding buffer, and 1 ml of serum was diluted with 3 ml of binding buffer. (The serum was sterile filtered prior to use.) The diluted serum (4 ml) was applied to the column and the wash was saved in a Corning tube. The column was washed with 10 mls of wash buffer. While the column was being washed, 200 µL of neutralization buffer was placed into 3 tubes. Elution buffer (6 ml) was applied to the column and one of the "neutralized" Corning tubes was used every 2 mL to collect the eluate. Binding buffer (10 ml) followed by 5 CVs of 20% ethanol was applied to the column, and the column was stored at 4° C.

The pH of one of the neutralized tubes was monitored on the first run to ensure the pH was near neutral. SDS-PAGE was run under reducing conditions on a 12% PAGE gel on the (1) serum (2) wash and (3-5) each of the 3 Corning tubes which should contain the IgGs of choice, (7) final column wash and (8) LMW. In addition, the UV absorbance at 280 nm of each of the elution tubes was measured to ascertain the aliquots containing the eluted IgG. Tubes with IgGs were pooled and concentrated, as needed, for the proceeding steps.

Purification of SPECIFIC IgGs Using a Cross-Linked Antigen Column

Reagents used were 500 mL of Coupling Buffer (MicroLink® kit): 0.1 M sodium phosphate; 0.15 M NaCl, pH 7.2; 500 ml of Ultrapure water; 100 µg of antigen (either recombinant A/Brisbane/10/2007 or A/Brisbane/59/2007 hemagglutinin—SinoBiological); 1 ml of purified IgGs. Equipment used included a MicroLink Protein Coupling Kit; 0.45 µm filter (or 0.8 µm); Amicon Ultra-0.5 mL concentrator; UV for $A_{280}$ measurements; 12% SDS Page gel and SDS reagents.

Coupling buffer was prepared by dissolving the dry blend in the 500 ml of pure water. Antigen was dissolved in 300 µl of the coupling buffer, reserving samples for both $A_{280}$ measurements and SDS PAGE. Manufacturer's instructions for coupling the antigen to the column were followed, and the column was washed and stored at 4° C. Purified IgG sample was concentrated to 200-300 µL The General Procedure for Affinity Purification was performed according to kit instructions. Concentrated IgGs were applied directly to the column. The slurry/IgG was incubated overnight at 4° C. Elution was performed 2-3 times after washing 3 times with PBS-T and 0.5 M NaCl and 3 times PBS-T. After elution, the column was washed 3 times with coupling buffer, and the flow through general IgG was reapplied and incubated with the antigen-specific column overnight. The same elution procedure was followed, and the process was repeated one additional time. Elutions were pooled and concentrated using an Amicon Ultra-0.5 mL concentrator. A portion of the concentrated antigen-specific sample was applied to a 12% SDS PAGE gel under reducing conditions and with precautions to avoid keratin contamination. Heavy chain and light chain bands were excised and sent to Prottech for LC MS/MS analysis with the repertoire sequencing database.

Antigen-Specific IgG Fab Preparation

Reagents used were: Pierce Fab Micro Preparation Kit; 12% BioRad Ready Gel; 0.5 mL eppendorf tubes, autoclaved; SDS reagents.

The other portion of the concentrated antigen-specific IgGs were applied to the Pierce Fab Micro Preparation Kit, and the kit instructions for isolating the Fab fragments were followed. Basically, the IgG was run through a column with immobilized papain, which cleaves at the flexible hinge. The flow-through was run through an immobilized Protein A column and saved. The Fc region remained bound to the column (the Protein A) but the Fab arms (disulfide bonded) eluted in the flow-through.

The flow through from the protein A column was concentrated using an Amicon Ultra-0.5 ml concentrator, and SDS PAGE was performed under reducing conditions and with precautions to avoid keratin contamination. The light chain and heavy chain fragments overlap on the gel with both running at approximately 25 kDa. The band that corresponds to the Fab fragment was cut and subjected to tandem LC MS analysis with ProtTech.

ELISA Protocol

Reagents used included: Binding buffer. Sodium bicarbonate buffer, 50 mM pH 9.6; Wash Buffer: PBS-T (PBS containing 0.05% Tween-20); Blocking Buffer: Pierce StartingBlock®; Stop Acid: 2 N $H_2SO_4$ or 3N HCl; 100 ug lyophilized recombinant hemagglutinin (A/Brisbane/10/ 2007 and/or A/Brisbane/50/2007 hemagglutinin); Rabbit anti-cmyc-HRP conjugated antibody (1:1000); Rabbit anti-FLAG-HRP conjugated antibody (1:1000); 1 step UltraTMB.

Plates were prepared by resuspending lyophilized recombinant hemagglutinin (either A/Brisbane/59/2007 or A/Brisbane/10/2007) in ultra-pure water to a final concentration of 200 ug/ml, followed by adding 100 ul of 0.5 ug/mL antigen in sodium bicarbonate buffer pH 9.6 to each well of a Polysorp plate (Nunc). Plates were incubated overnight at 4° C. Plates were washed 6× with PBS-T (300 ul per wash) and blocked for 30 min using StartingBlock buffer (Pierce). (Plates can be stored dry at 4° C. for up to one year at this point.) 100 µl of antigen-specific solution was added to each plate and incubated overnight at 4° C.

Antigen-Specific Fab Fragment Detection and Measurement

Plates were washed 6× with PBS-T (300 ul per wash) to remove unbound Fab. 100 ul of a mixture of 1:1000 anti-cmyc and anti-FLAG in PBS-T were added to each well of the plate, and plates were incubated at room temperature for 3 hours. Unbound conjugate was removed by washing the plate 6× with PBS-T. 100 uL of 1-step TMB ultra was added to each well and allowed to react for up to 30 minutes. The reaction was stopped by adding 50 uL of 1M $H_2SO_4$ and the plate was promptly read at 450 nm.

Antigen-Specific In Vitro Stimulation of Human PBMCs

The objective was to stimulate proliferation and differentiation of antigen-specific human peripheral blood mononuclear cells (PBMCs) in vitro in order to assess the response using high-throughput sequencing.

Reagents used were: RPMI-1640 media supplemented with 4 mM L-glutamine; 10% heat-inactivated FCS/FBS (fetal bovine serum); 50 U/ml penicillin; 50 µg/ml streptomycin; and Phosphate Buffered Saline (PBS) solution. Antigen used was 200 ug/ml recombinant hemagglutinin A/Brisbane/59/2007.

Whole blood (8 ml) was drawn into a CPT vacutainer tube. The peripheral blood mononuclear cells (PBMC) layer was isolated and washed to remove any serum antigen which could interfere with downstream ELISA. Blood serum was stored at −80° C. for later analysis.

At least 100 mL of sterile supplemented RPMI media was prepared and the media was aliquoted into 4-6 ml Corning tubes. Antigen was added to each of the Corning tubes to prepare a range of antigen concentrations with which to challenge the PBMC in vitro including 0 ug/ml (unchallenged sample), 0.02 ug/ml, 0.2 ug/ml and 2 ug/ml. This media (2-ml per 3 wells) was placed into each well of a 3×4 cell culture plate, and $2 \times 10^6$ PBMCs were plated per well. Plates were then incubated in a $CO_2$ incubator under humidified conditions with 5% $CO_2$, at 37° C. Cells were monitored for growth and health by Trypan staining every other day. Fresh media was added as required every other day, reserving 100 µl of media daily for ELISA analysis. Cells were harvested on day 11 using the citric-saline method with gentle agitation and a small rubber spatula.

Mononuclear Cell Isolation

Buffer A was prepared by making a 1 L solution of PBS with 6 grams of Sodium Citrate and 0.1% FCS (1 ml FCS/1 L). Blood (8 ml) was drawn into a CPT vacutainer tube and the tube was centrifuged for 15 minutes at 1500 RCF at room temperature in a swinging bucket centrifuge. After centrifuging, tubes were gently inverted 5-10 times. The vacutainer was opened, and the entire plasma fraction was removed and placed into a new 15 ml conical tube. The total volume was increased to 15 ml by the addition of an appropriate quantity of Buffer A, and tubes were inverted gently 5 times. Tubes were centrifuged for 15 minutes at 300 RCF at room temperature. Supernatant was removed and volume adjusted to 10 ml using Buffer A. Tubes were gently inverted 5 times, and this step was repeated one time. Tubes were centrifuged for 10 minutes at 300 RCF at room temperature. Supernatant was removed and the cell pellet re-suspended to desired volume. Tube contents were gently mixed using a pipette.

What is claimed is:

1. A method for identifying antigen-specific T cells, the method comprising:
   a) obtaining a sample of blood or tissue from a human subject that has been previously challenged with a disease-associated-antigen in vivo;
   b) isolating peripheral blood mononuclear cells, wherein the peripheral blood mononuclear cells comprise T cells, from the sample and culturing the peripheral blood mononuclear cells in vitro;
   c) adding an effective amount of the antigen to a portion of the peripheral blood mononuclear cells in vitro;
   d) harvesting RNA from the peripheral blood mononuclear cells at an empirically-determined time after adding the antigen;
   e) amplifying the harvested RNA using arm-PCR and sequencing the resulting amplicons to generate an immunorepertoire for T cells stimulated with the antigen in vitro and for T cells not stimulated with the antigen in vitro; and
   f) diagnosing the human subject with disease associated with the antigen where an increase in one or more T cell clones is detected in the T cells stimulated with the antigen in vitro but is not detected in the T cells not stimulated with the antigen in vitro.

2. The method of claim 1, further comprising diagnosing the human subject with influenza where an increase in one or more T cell clones is detected in the T cells stimulated with the antigen in vitro but is not detected in the T cells not stimulated with the antigen in vitro, wherein the antigen is hemagglutinin.

* * * * *